(12) United States Patent
Ahmad et al.

(10) Patent No.: US 10,694,966 B1
(45) Date of Patent: *Jun. 30, 2020

(54) LEADLESS ECG MONITORING VIA ELECTRODE SWITCHING

(71) Applicant: The Access Technologies, Ottawa (CA)

(72) Inventors: Saif Ahmad, Kanata (CA); Atul Kumar Garg, Kanata (CA)

(73) Assignee: The Access Technologies, Ottawa, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/514,727

(22) Filed: Jul. 17, 2019

Related U.S. Application Data

(63) Continuation-in-part of application No. 16/353,894, filed on Mar. 14, 2019, now Pat. No. 10,463,302.

(30) Foreign Application Priority Data

Mar. 8, 2019 (CA) ..................................... 3036168

(51) Int. Cl.
| | | |
|---|---|---|
| *A61B 5/0408* | (2006.01) | |
| *A61B 5/00* | (2006.01) | |
| *A61B 5/044* | (2006.01) | |

(52) U.S. Cl.
CPC ............ *A61B 5/0408* (2013.01); *A61B 5/044* (2013.01); *A61B 5/681* (2013.01)

(58) Field of Classification Search
CPC . A61B 5/681; A61B 5/04017; A61B 5/04085; A61B 5/0456; A61B 5/6828;
(Continued)

(56) References Cited

U.S. PATENT DOCUMENTS

| 5,289,824 A | 3/1994 | Mills et al. |
|---|---|---|
| 7,460,899 B2 | 12/2008 | Almen |

(Continued)

FOREIGN PATENT DOCUMENTS

| CN | 108433718 A | 8/2018 |
|---|---|---|
| WO | WO2019042486 A1 | 3/2019 |

OTHER PUBLICATIONS

High resolution ambulatory electrocardiographic monitoring using wrist-mounted electric potential sensors, CJ Harland et al., 2003, Meas. Sci. Technol. 14 923.

(Continued)

*Primary Examiner* — Paula J Stice
(74) *Attorney, Agent, or Firm* — Faegre Drinker Biddle & Reath LLP

(57) ABSTRACT

An ergonomically designed wireless wearable smart band pair for continuous ECG monitoring is disclosed. The pair comprises primary and secondary smart bands with integrated electrodes that are provided with switches for enabling desired electrodes during data acquisition. When the smart bands are worn around the two limbs, electrodes contact the skin. The primary smart band sets all possible states of the electrode switches and acquires biopotential data from the first wrist while the secondary smart band simultaneously acquires biopotential data from the second wrist and sends it wirelessly to the primary smart band. The primary smart band processes biopotential data via digital and analog signal conditioning and fuses information to acquire high-fidelity ECG data as per Einthoven's law without need for completing a circuit via leads and/or holding auxiliary electrodes. The primary smart band analyzes ECG data in real-time, generates pertinent alarms, stores data locally, and wirelessly transmits information to external devices.

14 Claims, 11 Drawing Sheets

(58) Field of Classification Search
CPC ....... A61B 5/0006; A61B 5/044; A61B 5/046; A61B 5/6823
See application file for complete search history.

(56) References Cited

U.S. PATENT DOCUMENTS

| | | |
|---|---|---|
| 7,894,888 B2 | 2/2011 | Chan et al. |
| 8,527,038 B2 | 9/2013 | Moon et al. |
| 9,655,537 B2 | 5/2017 | Bardy et al. |
| 9,706,922 B2 | 7/2017 | Cao |
| 9,844,340 B2 | 12/2017 | Fish et al. |
| 9,955,887 B2 | 5/2018 | Hughes et al. |
| 10,045,708 B2 | 8/2018 | Dusan |
| 2011/0319777 A1 | 12/2011 | Mehrotra et al. |
| 2016/0028269 A1 | 1/2016 | Miller et al. |
| 2016/0317067 A1 | 11/2016 | Lee |
| 2017/0020444 A1 | 1/2017 | Lurie |
| 2017/0055869 A1 | 3/2017 | Shin et al. |
| 2018/0345078 A1 | 12/2018 | Blahnik et al. |

OTHER PUBLICATIONS

Canadian Patent Office, "Examination Report", in published Canadian Patent Application No. 3,036,168, dated Jun. 14, 2019, 4 pages.

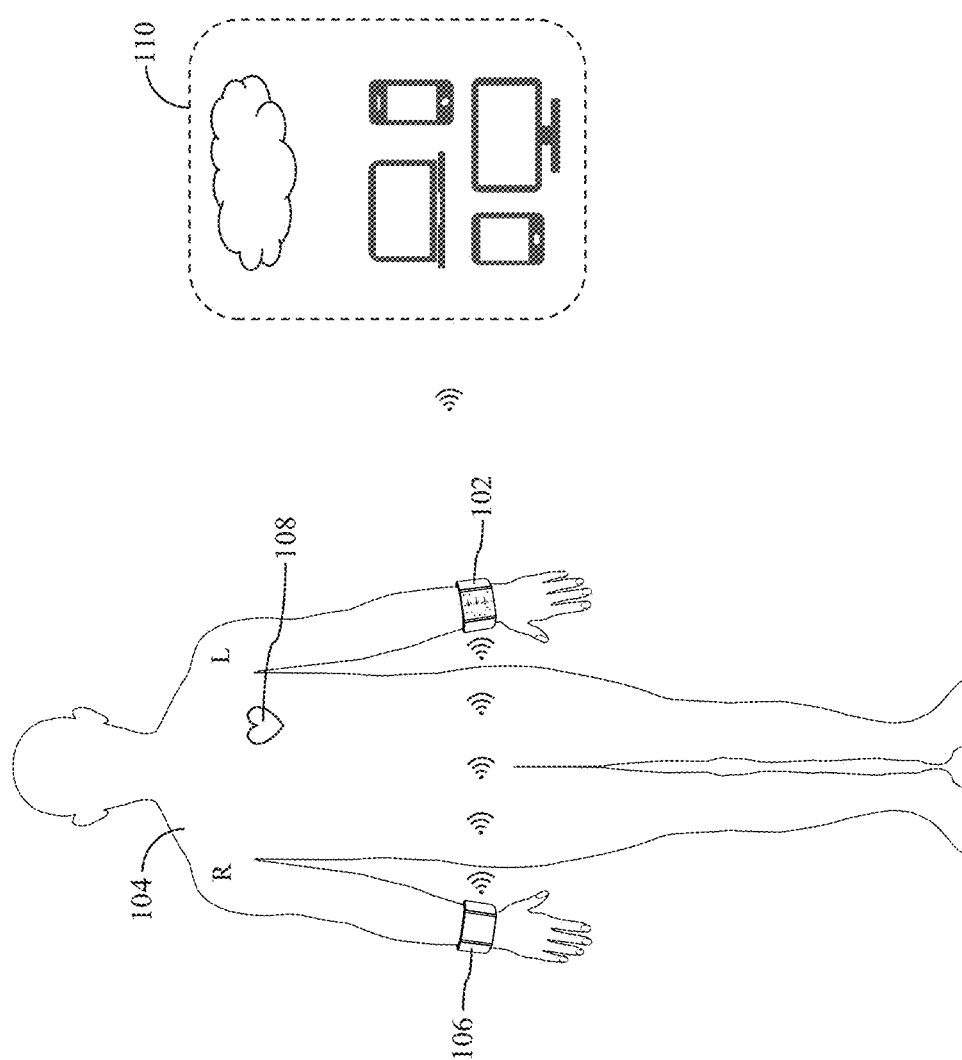

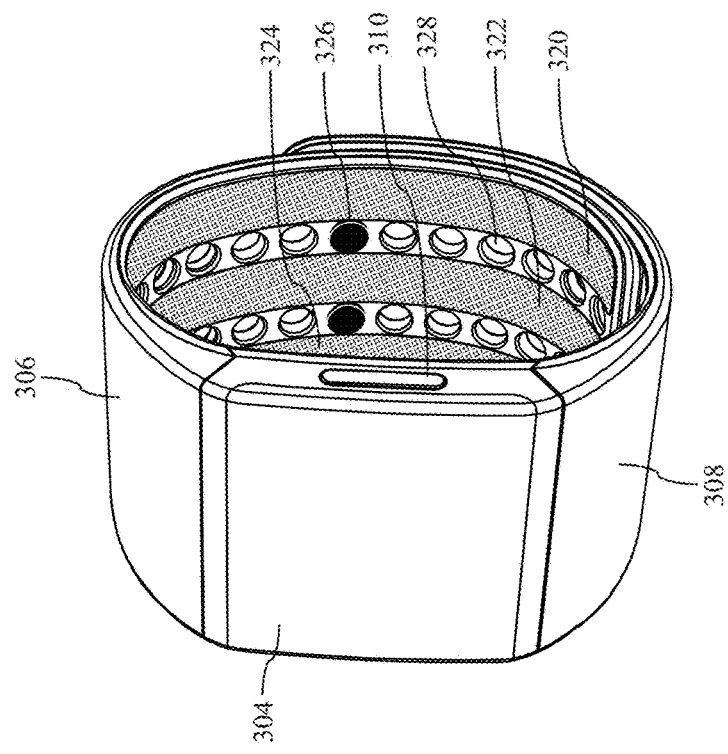
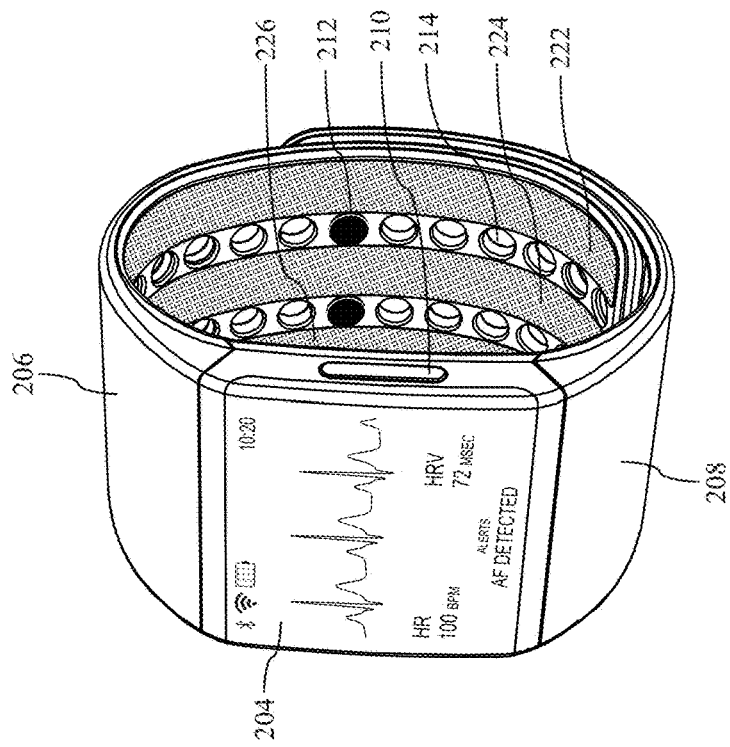
FIG. 5
FIG. 4

| # | Secondary Smart Band | | | Primary Smart Band | | | |
|---|---|---|---|---|---|---|---|
| | $S_{LS}$ | $S_{BS}$ | $S_{OS}$ | $S_{LP}$ | $S_{BP}$ | $S_{OP}$ | |
| 2 | 0 | 0 | 0 | 0 | 0 | 1 | |
| 3 | 0 | 0 | 0 | 0 | 1 | 0 | |
| 4 | 0 | 0 | 0 | 0 | 1 | 1 | |
| 5 | 0 | 0 | 0 | 1 | 0 | 0 | |
| 6 | 0 | 0 | 0 | 1 | 0 | 1 | |
| 7 | 0 | 0 | 0 | 1 | 1 | 0 | |
| 8 | 0 | 0 | 0 | 1 | 1 | 1 | |
| 9 | 0 | 0 | 1 | 0 | 0 | 0 | |
| 10 | 0 | 0 | 1 | 0 | 0 | 1 | |
| 11 | 0 | 0 | 1 | 0 | 1 | 0 | |
| 12 | 0 | 0 | 1 | 0 | 1 | 1 | |
| 13 | 0 | 0 | 1 | 1 | 0 | 0 | |
| 14 | 0 | 0 | 1 | 1 | 0 | 1 | |
| 15 | 0 | 0 | 1 | 1 | 1 | 0 | |
| 16 | 0 | 0 | 1 | 1 | 1 | 1 | |
| 17 | 0 | 1 | 0 | 0 | 0 | 0 | |
| 18 | 0 | 1 | 0 | 0 | 0 | 1 | |
| 19 | 0 | 1 | 0 | 0 | 1 | 0 | |
| 20 | 0 | 1 | 0 | 0 | 1 | 1 | |
| 21 | 0 | 1 | 0 | 1 | 0 | 0 | |
| 22 | 0 | 1 | 0 | 1 | 0 | 1 | |
| 23 | 0 | 1 | 0 | 1 | 1 | 0 | |
| 24 | 0 | 1 | 0 | 1 | 1 | 1 | |
| 25 | 0 | 1 | 1 | 0 | 0 | 0 | |
| 26 | 0 | 1 | 1 | 0 | 0 | 1 | |
| 27 | 0 | 1 | 1 | 0 | 1 | 0 | |
| 28 | 0 | 1 | 1 | 0 | 1 | 1 | |
| 29 | 0 | 1 | 1 | 1 | 0 | 0 | |
| 30 | 0 | 1 | 1 | 1 | 0 | 1 | |
| 31 | 0 | 1 | 1 | 1 | 1 | 0 | |
| 32 | 0 | 1 | 1 | 1 | 1 | 1 | |

FIG. 10A

| # | Secondary Smart Band | | | Primary Smart Band | | | |
|---|---|---|---|---|---|---|---|
| | $S_{LS}$ | $S_{BS}$ | $S_{OS}$ | $S_{LP}$ | $S_{BP}$ | $S_{OP}$ | |
| 33 | 1 | 0 | 0 | 0 | 0 | 0 | |
| 34 | 1 | 0 | 0 | 0 | 0 | 1 | |
| 35 | 1 | 0 | 0 | 0 | 1 | 0 | |
| 36 | 1 | 0 | 0 | 0 | 1 | 1 | |
| 37 | 1 | 0 | 0 | 1 | 0 | 0 | |
| 38 | 1 | 0 | 0 | 1 | 0 | 1 | |
| 39 | 1 | 0 | 0 | 1 | 1 | 0 | |
| 40 | 1 | 0 | 0 | 1 | 1 | 1 | |
| 41 | 1 | 0 | 1 | 0 | 0 | 0 | |
| 42 | 1 | 0 | 1 | 0 | 0 | 1 | |
| 43 | 1 | 0 | 1 | 0 | 1 | 0 | |
| 44 | 1 | 0 | 1 | 0 | 1 | 1 | |
| 45 | 1 | 0 | 1 | 1 | 0 | 0 | |
| 46 | 1 | 0 | 1 | 1 | 0 | 1 | |
| 47 | 1 | 0 | 1 | 1 | 1 | 0 | |
| 48 | 1 | 0 | 1 | 1 | 1 | 1 | |
| 49 | 1 | 1 | 0 | 0 | 0 | 0 | |
| 50 | 1 | 1 | 0 | 0 | 0 | 1 | |
| 51 | 1 | 1 | 0 | 0 | 1 | 0 | |
| 52 | 1 | 1 | 0 | 0 | 1 | 1 | |
| 53 | 1 | 1 | 0 | 1 | 0 | 0 | |
| 54 | 1 | 1 | 0 | 1 | 0 | 1 | |
| 55 | 1 | 1 | 0 | 1 | 1 | 0 | |
| 56 | 1 | 1 | 0 | 1 | 1 | 1 | |
| 57 | 1 | 1 | 1 | 0 | 0 | 0 | |
| 58 | 1 | 1 | 1 | 0 | 0 | 1 | |
| 59 | 1 | 1 | 1 | 0 | 1 | 0 | |
| 60 | 1 | 1 | 1 | 0 | 1 | 1 | |
| 61 | 1 | 1 | 1 | 1 | 0 | 0 | |
| 62 | 1 | 1 | 1 | 1 | 0 | 1 | |
| 63 | 1 | 1 | 1 | 1 | 1 | 0 | |

FIG. 10B

LEADLESS ECG MONITORING VIA ELECTRODE SWITCHING

RELATED APPLICATIONS

This application is a continuation-in-part of U.S. patent application Ser. No. 16/353,894, filed Mar. 14, 2019, now U.S. Pat. No. 10,463,302, the disclosure of which is expressly incorporated by reference herein. This application further claims priority to Canadian Patent Application No. 3,036,168, filed Mar. 8, 2019, the disclosure of which is expressly incorporated by reference herein.

TECHNICAL FIELD

In general, this invention relates to electrocardiogram (ECG) monitoring in humans with wearable technology, and in particular to continuous and unobtrusive ECG monitoring utilizing a pair of ergonomically designed wireless smart bands that the user wears around the left and right wrists.

BACKGROUND

A regular ECG test is an essential diagnostic tool that characterizes the heart's activity at a given point in time. Abnormal heart rhythms and cardiac symptoms may however sporadically appear, disappear, and reappear over time. Consequently, point-in-time ECG tests may miss critical cardiac anomalies, thereby leading to an increased risk of morbidity and mortality.

It is therefore important to monitor ECG continuously in at-risk patients as they go about their normal activities. Quite often, serious heart conditions like atrial fibrillation (AF), cardiomyopathy, and coronary heart disease are diagnosed with continuous ECG monitoring. This allows for timely clinical interventions like medication and cardiac surgery that reduce adverse outcomes like stroke and heart attack, thereby saving lives.

In clinical practice, it is common to undertake continuous ECG monitoring using a Holter system that can generally record 24-48 hours of cardiac data. The Holter is a small wearable biopotential measurement device comprising several ECG leads. These ECG leads are snapped on to sticky gel electrodes that are attached at various locations on the patient's chest. A Holter monitoring system is inconvenient and obtrusive due to the sticky gel chest electrodes that often cause discomfort and the unwieldy leads that hang between the electrodes and the Holter unit.

Recently, Medtronic has developed and marketed a leadless Holter system (SEEQ™) in the form of an adhesive chest strip (~4.5" long, ~2.0" wide, and ~0.6" thick) for continuous ECG monitoring. Though leadless, this monitor is awkward and uncomfortable because it uses sticky chest electrodes and it is too bulky to be attached to the chest.

Various kinds of belts that can be worn around the chest for continuous ECG monitoring are available in the market today. Many of these ECG chest belt systems are leadless and employ dry reusable electrodes. Still, these ECG belts need to be worn under clothing and are often quite tight around the chest, causing difficulty and uneasiness to the wearer.

Currently, continuous ECG monitoring technology comes with a number of problems and encumbrances. These include discomfort, uneasiness, sleep disruptions, difficulty in carrying out day-to-day activities, and inability to undertake long-term monitoring (for example, monitoring for days, months, and years).

With the advent of newer generation wearables like smartwatches, attempts have been made to integrate ECG monitoring into a smartwatch. For example, Apple has provided dry ECG electrodes on the backplate of a smartwatch (left-side electrodes) and a second set of electrodes on the smartwatch rim (right-side electrodes). A user has to wear the smartwatch on one wrist so that the electrodes underneath touch the wrist. Additionally, the user has to touch the second set of electrodes on the smartwatch rim with his/her other hand so that the heart lies in-between the left-side (backplate) and right-side (rim) electrodes that are electrically connected to signal amplification/conditioning circuitry inside the smartwatch. The quality of ECG data acquired in this manner is generally satisfactory. However, the main limitation is that the user has to touch and hold a second set of electrodes on the smartwatch with his/her other hand for monitoring ECG data. As a result, this system only provides an on demand 30 seconds of ECG monitoring, and not continuous and/or long-term ECG monitoring.

To avoid touching a second set of electrodes with the other hand and to accomplish leadless continuous ECG monitoring, attempts have been made to develop wearable single upper limb ECG systems.

Prior art has proposed the use of single arm wearable devices for leadless ECG monitoring. These systems comprise an upper arm band with more than one electrode on the underside that come in contact with the arm when the band is worn. The electrodes are interfaced with an amplification and control unit that may be affixed to the outer surface of the band. Single arm ECG systems have produced mixed results for a diverse population. The ECG signal acquired by these systems is often noisy, unreliable, and unusable, more so for women and older people.

Based on the principles of single arm ECG systems, other prior art has also proposed leadless ECG monitoring employing wearable single wrist systems. The quality and fidelity of data acquired by single wrist ECG systems has not been properly tested and/or verified. Intuitively, a single wrist ECG system will produce noisier and weaker signals as compared to a single arm ECG system. This is because the wrist is physically farther away from the heart as compared to the upper arm, thus resulting in greater impedance to the flow of electrical charge from the heart to the wrist electrodes.

SUMMARY

In one aspect of the present invention there is disclosed a wearable device related to ECG monitoring technology. The wearable device comprises a pair of ergonomically designed wireless smart bands that are worn around the left and right wrists for unobtrusive continuous leadless ECG data monitoring and analysis. Both smart bands in the described pair are provided with dry reusable ECG electrodes on their underside. The electrodes in each smart band are interfaced with biopotential measurement hardware and software inside that smart band. Moreover, the hardware and software inside the two smart bands enables seamless wireless communication between them. When the two smart bands are worn on both hands, their respective electrodes come in contact with the left and right side of the body. With this configuration, the two smart bands independently and simultaneously measure biopotential on the left and right side of the body and wirelessly share/process this information to acquire/analyze high-fidelity ECG data. Thus, the wireless smart band pair accomplishes ECG data monitoring and analysis as per Einthoven's law without the need for physically completing a circuit via leads and/or touching and holding auxiliary electrodes.

The two smart bands in the described pair are alluded to as a primary smart band and a secondary smart band. Both the primary and secondary smart bands preferably comprise electrodes, ECG amplification/conditioning circuitry, a microcontroller, a wireless transceiver, and a rechargeable battery. The primary smart band can be additionally provided with memory and a touchscreen display. Both the primary and secondary smart bands preferably have wireless charging capabilities and can be charged on a twin wireless charging unit.

In one embodiment, both primary and secondary smart bands are provided with three ECG strip electrodes on their underside to maximize the electrode surface area and enhance connectivity around the wrist to obtain high-quality ECG signal. Each of the three strip electrodes can be arranged to have a rigid section on the smart band backplate and a flexible section along the underside of the smart band straps. In one example, the rigid electrodes are made of silver while the flexible electrodes are made of conductive fabric.

In one example, in both smart bands, the first strip is a right-side electrode and the second strip is a left-side electrode connected to a biopotential amplifier while the third strip is a reference electrode. In another example, in both smart bands, the right-side and left-side strip electrodes remain unchanged while the third strip or the reference electrode is a ground electrode. In yet another example, in both smart bands, the right-side and left-side strip electrodes remain unchanged while the third strip or the reference electrode is a right leg drive (RLD) electrode to reduce common mode noise and augment ECG signal quality. Finally, in another example, in both smart bands, the right-side and left-side strip electrodes remain unchanged while the third strip or reference electrode in the secondary smart band is a ground electrode and the third strip or reference electrode in the primary smart band is an RLD electrode for enhancing ECG data quality.

In one example, the primary smart band is worn around the left wrist while the secondary smart band is worn around the right wrist. With this setup, the primary smart band acquires biopotential data from the left side of the body. Simultaneously, the secondary smart band acquires biopotential data from the right side of the body and transmits this information wirelessly to the primary smart band. Biopotential information from the left and right side of the body is processed and combined inside the primary smart band using a variety of methods to acquire high-fidelity ECG signal.

In one embodiment, inside each smart band, a digital switch is provided between each of the three strip electrodes and the associated signal amplification/conditioning circuitry, resulting in three digital electrode switches inside each smart band. In another embodiment, the digital switch of the third strip or reference electrode in each smart band is a changeover switch that is used to convert the reference electrode into either a ground or RLD electrode. In one example, all digital switches inside the two smart bands are controlled by the respective microcontrollers inside the smart bands. These electrode switches allow various electrode configurations to be evaluated and used for enhancing ECG data quality. This feature is useful for device testing and calibration whereby an optimum electrode configuration that results in best ECG signal quality can be readily determined and employed. In an example configuration, all three electrodes, namely, right, left, and RLD of the primary smart band are enabled while only right and left electrodes of the secondary smart band are enabled.

Factors like individual physiology, electrode contact area, mechanical pressure on electrodes, and electrode vibration may introduce noise in the left and right side biopotential data acquired by the smart band pair. Therefore, the resulting ECG signal may also be contaminated with noise. In such scenarios, the digital switches that allow different configurations of the six electrodes of the two smart bands to be used during data acquisition can be employed to reduce noise for obtaining a high-fidelity ECG signal. However, for a given operating condition (for example, mechanical pressure on the electrodes), a particular electrode configuration may give best results whereas for another operating condition (for example, electrode vibration), a different electrode configuration may produce better results. To overcome this limitation, in one embodiment, rapid switching of the six digital switches of the two smart bands is undertaken such that left and right side biopotential data is acquired and combined every data sampling period as the system continuously and repeatedly loops through all possible electrode configurations to minimize noise and enhance signal quality under all operating conditions.

In one example, the biopotential data from both smart bands is sent directly to the microcontroller inside the primary smart band whereby various digital signal processing (DSP) techniques are employed to obtain an ECG signal. In another example, the biopotential data from both smart bands is first sent to a differential amplifier for analog signal amplification and conditioning, and then to the microcontroller inside the primary smart band for processing and obtaining an ECG signal. In yet another example, the ECG information obtained via the DSP and analog signal amplification/conditioning techniques is fused by the microcontroller inside the primary smart band to obtain an ECG signal of even higher quality and fidelity.

In a further aspect, the microcontroller inside the primary smart band analyzes acquired ECG data in real-time to compute parameters like heart rate (HR) and heart rate variability (HRV) and to generate alerts when these parameters are out of range. For example, if HRV is above a given threshold, an AF alert is generated. The primary smart band displays real-time ECG waveform data along with metrics like HR and HRV and any alerts that are generated. The onboard memory in the primary smart band stores all ECG-related information. The primary smart band can also have the functionality to send all acquired ECG data and related information wirelessly to a smartphone, personal computer (PC), tablet, or directly to a cloud server where it can be further processed/analyzed.

Though this invention is described as related to a pair of wearable smart bands that are attached to a user's left and right wrists, the underlying design and principle of the invention can be extended to a pair of wearables that can be attached at any location along the two upper limbs and/or even the two lower limbs. One example comprises a primary smart band worn around the wrist and a secondary smart band worn around the upper arm of the other hand. Another example comprises both primary and secondary smart bands worn around the two upper arms. Yet another example comprises a primary smart band worn around the wrist and a secondary smart band worn around the ankle of the other leg. It will be appreciated that the smart band could be a smartwatch or any other similar wearable.

This invention fulfills the theoretical underpinnings of electrocardiography and Einthoven's law such that biopotential is measured on the left and right sides of the body with the heart in-between utilizing a pair of wirelessly synced wearables (for example, smart bands, smartwatches, and/or any combination thereof) that process all information to acquire high-fidelity single-lead ECG waveform data.

In accordance with one aspect, there is provided an electrocardiogram monitor comprising: a primary smart band having a primary microcontroller, at least three electrodes, and at least one digital switch per electrode to enable or disable the electrode during data acquisition, wherein the at least three electrodes are configured to contact skin of a user and measure a first high-fidelity biopotential signal; a secondary smart band having a secondary microcontroller, at least three electrodes, and at least one digital switch per electrode to enable or disable the electrode during data acquisition, wherein the at least three electrodes are configured to contact the skin of the user and measure a second high-fidelity biopotential signal; wherein the primary and secondary microcontrollers control the digital switches to repeatedly loop through all possible configurations of the digital switches and acquire first and second high-fidelity biopotential signals for each configuration; wherein, for each configuration of the digital switches, the secondary microcontroller digitizes the second high-fidelity biopotential signal to produce a second digitized signal and transmits the second digitized signal wirelessly to the primary smart band; wherein, for each configuration of the digital switches, the primary microcontroller wirelessly receives the second digitized signal from the secondary smart band, and digitizes the first high-fidelity biopotential signal to produce a first digitized signal; wherein the primary microcontroller aggregates the first and second digitized signals for all switch configurations and employs DSP techniques on the aggregated first and second digitized signals to produce a first high-fidelity ECG waveform signal; wherein the primary smart band further comprises a D/A module to convert the second digitized signal to an analog signal; and a differential amplifier which, for each configuration of the digital switches, receives as inputs the analog signal from the D/A module and the first high-fidelity biopotential signal and outputs a high-fidelity differential signal via analog signal conditioning and amplification; wherein the primary microcontroller digitizes and aggregates the high-fidelity differential signal for all switch configurations to produce a second high-fidelity ECG waveform signal; wherein the primary microcontroller employs data fusion techniques to combine the first and second high-fidelity ECG waveform signals to produce a higher quality and fidelity ECG waveform signal.

BRIEF DESCRIPTION OF THE DRAWINGS

FIG. 1 illustrates an exemplary attachment of the wireless smart band pair on a user for continuous leadless ECG monitoring along with external devices to which data is wirelessly transmitted.

FIG. 4 illustrates an alternate view of the primary smart band showing the touchscreen display along with the straps, clasping mechanism, and flexible strip electrodes.

FIG. 5 illustrates an alternate view of the secondary smart band showing the front cover along with the straps, clasping mechanism, and flexible strip electrodes.

FIGS. 10A-10B illustrates a truth table enlisting all possible states of the six electrode switches.

DETAILED DESCRIPTION

Figure 2C:
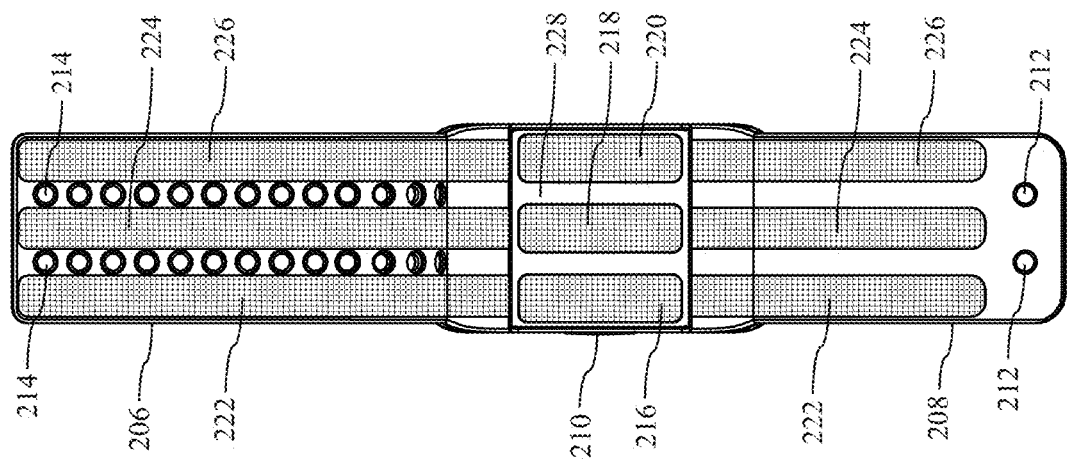
FIGS. 2A-2C illustrate the front, side, and back of the primary smart band showing the touchscreen display along with the rigid/flexible strip electrodes and clasping studs/holes.

A preferred embodiment of the present invention will be set forth in detail with reference to the drawings, in which like reference numerals refer to like elements or method steps throughout.

FIG. 1 illustrates an exemplary attachment of the wireless smart band pair on a user for continuous leadless ECG monitoring along with external devices to which data is wirelessly transmitted. In this example, the primary smart band 102 is worn by the user 104 around the left wrist whereas the secondary smart band 106 is worn around the right wrist. The heart 108 is shown inside the chest cavity positioned slightly towards the left. The secondary smart band 106 worn around the right wrist measures the right-side biopotential by virtue of the electrodes provided on its underside (not shown) and sends this information wirelessly to the primary smart band 102 worn around the left wrist. Simultaneously, the primary smart band 102 worn around the left wrist measures the left-side biopotential by virtue of the electrodes provided on its underside (not shown) and combines/processes this information with the wirelessly received right-side biopotential information to acquire high-fidelity ECG waveform data. The primary smart band 102 analyzes the acquired ECG data, stores all information locally, and also transmits this information wirelessly to remote devices 110 like smartphones, laptops, tablets, and cloud databases for storage and further analysis. The primary 102 and secondary 106 smart bands can also be swapped between the two hands to acquire ECG data in a manner similar to the one described above. That is, the primary smart band 102 can be also worn around the right wrist and the secondary smart band 106 can also be worn around the left wrist for continuous leadless ECG monitoring as outlined in the invention.

Figure 2B:
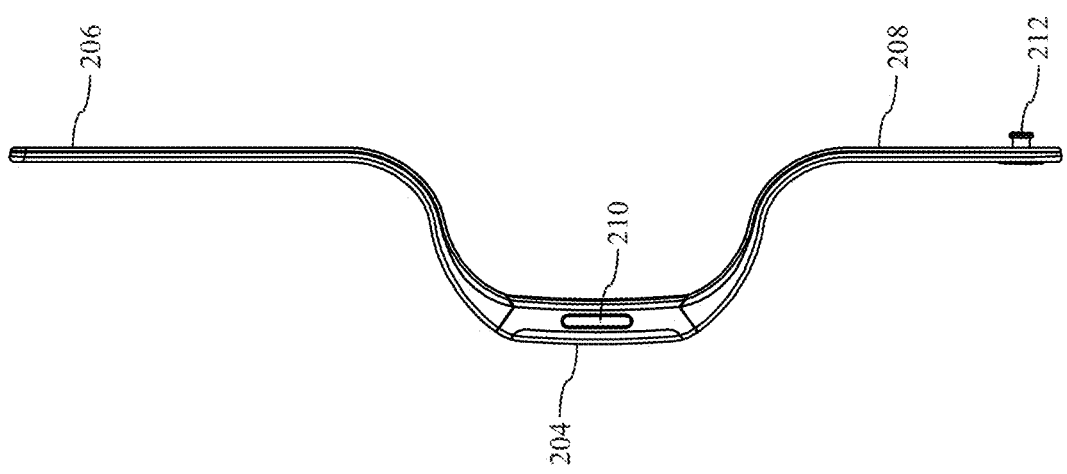
Figure 2A:
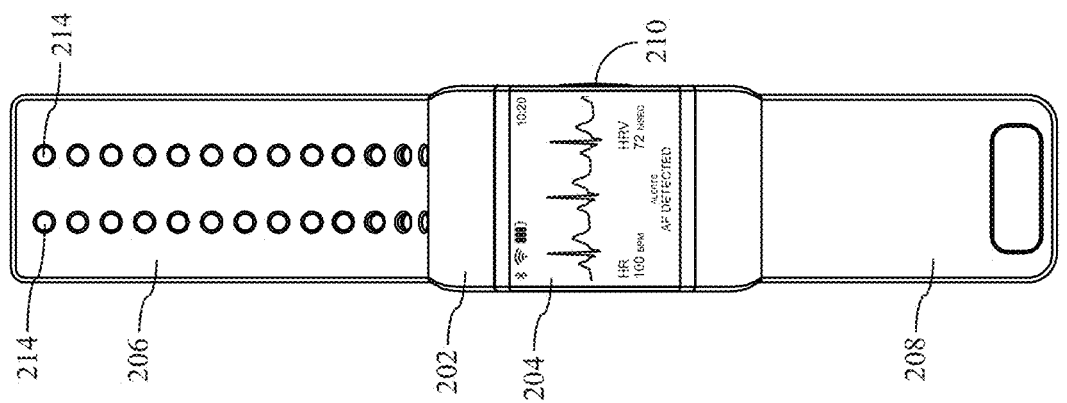

FIGS. 2A-2C illustrate one embodiment of the front, side, and back of the primary smart band showing the touchscreen display along with the rigid/flexible strip electrodes and clasping studs/holes. The primary smart band comprises an enclosure 202 made of stainless steel, a touchscreen display 204, upper 206 and lower 208 straps made of flexible rubber, and an on/off button 210. Studs 212 made of hard rubber and corresponding holes 214 are provided on the primary smart band straps for clasping it snugly around the wrist. It will be appreciated that while two sets of studs 212 and holes 214 are shown, a single set, multiple sets or other arrangements could be used instead. It will also be appreciated that the display 204 could be a plain display that is not a touchscreen.

Three rigid strip electrodes 216, 218, 220 and three flexible strip electrodes 222, 224, 226 are provided on the underside of the primary smart band. The three rigid strip electrodes 216, 218, 220 are embedded in the primary smart band backplate 228 that is made of plastic. The three flexible strip electrodes 222, 224, 226 are embedded in the upper 206 and lower 208 straps of the smart band. Each of the three rigid 216, 218, 220 and flexible 222, 224, 226 strip electrodes are electrically connected inside the primary smart band. That is rigid strip electrode 216 is connected to flexible strip electrode 222, rigid strip electrode 218 is connected to flexible strip electrode 224, and rigid strip electrode 220 is connected to flexible strip electrode 226. In one example, the rigid strip electrodes 216, 218, 220 are made of silver while the flexible strip electrodes 222, 224, 226 are made of silver foil. In another example, the rigid strip electrodes 216, 218, 220 are made of chrome-plated steel while the flexible strip electrodes 222, 224, 226 are made of conductive fabric. A variety of conductive materials can be used to fabricate the rigid and flexible strip electrodes described in this invention.

In one example, the approximate dimensions of the primary smart band enclosure 202 are 43.0 mm (length)×42.0 mm (width)×9.5 mm (height). The width of the straps 206, 208 is approximately 41.0 mm and closely matches the length of the smart band enclosure 202. The approximate width of the rigid 216, 218, 220 and flexible 222, 224, 226 strip electrodes is 8.5 mm and the approximate separation between them is 5.5 mm. In this example, the 5.5 mm gap between the flexible strip electrodes 222, 224, 226 conveniently allows for the primary smart band clasping studs 212 and holes 214 to be provided within this gap. The approximate weight of such a primary smart band is 40 g.

Figure 3C:
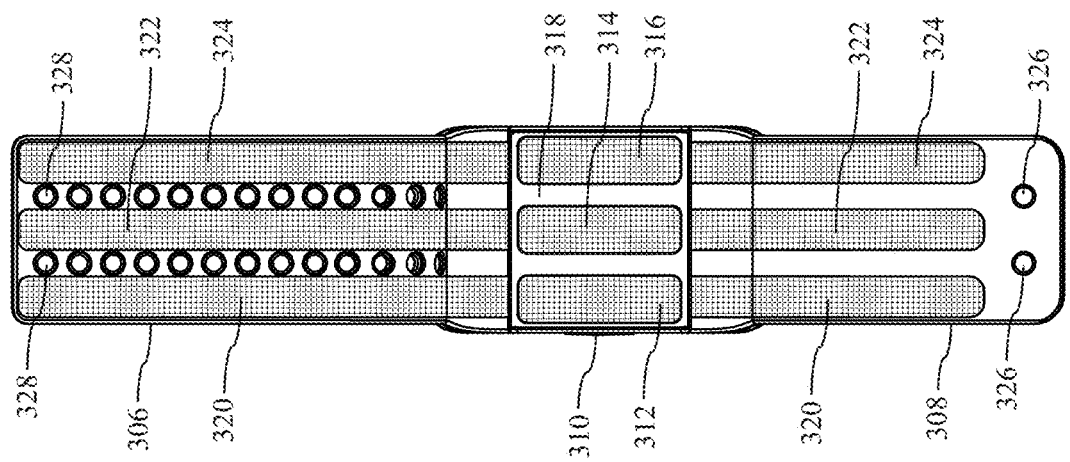
FIGS. 3A-3C illustrate the front, side, and back of the secondary smart band showing the front cover along with the rigid/flexible strip electrodes and clasping studs/holes.
Figure 3B:
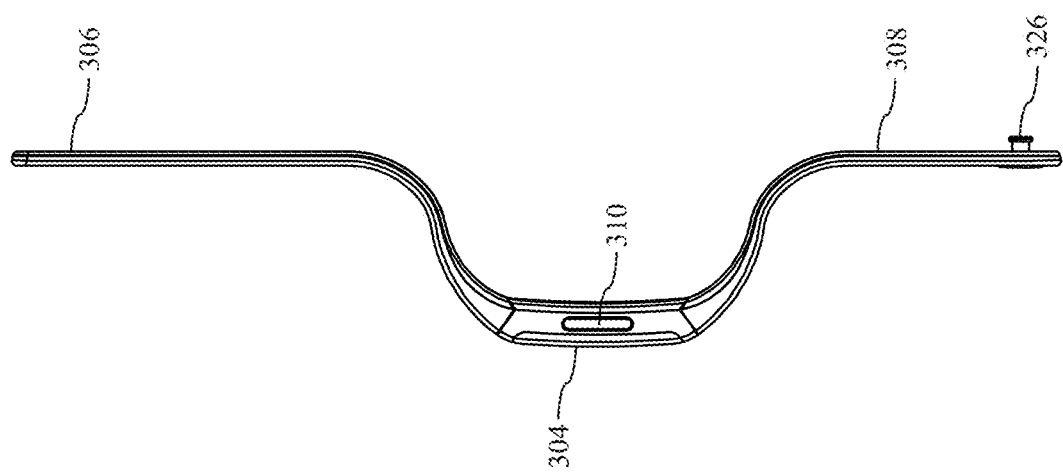
Figure 3A:
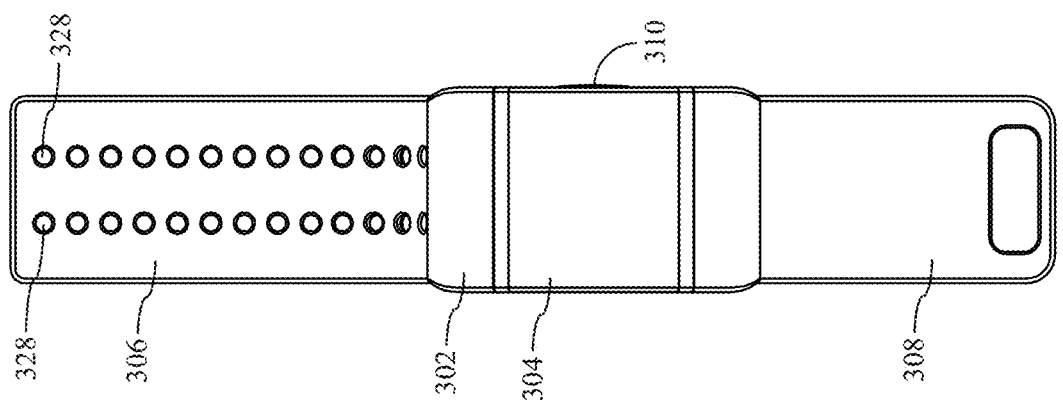

FIGS. 3A-3C illustrate one embodiment of the front, side, and back of the secondary smart band showing the front cover along with the rigid/flexible strip electrodes and clasping studs/holes. The design, footprint, materials, dimensions, weight, and fabrication of the secondary smart band is similar to that of the primary smart band. The only difference is that the secondary smart band does not have a display. In this example, the secondary smart band comprises an enclosure 302 made of stainless steel, a plastic front cover 304, upper 306 and lower 308 straps made of flexible rubber, and an on/off button 310. It also comprises three rigid strip electrodes 312, 314, 316 embedded in a plastic backplate 318 and three flexible strip electrodes 320, 322, 324 embedded in the upper 306 and lower 308 straps. Studs 326 made of hard rubber and holes 328 are provided on the secondary smart band straps for clasping it snugly around the wrist. It will be appreciated that while two sets of studs 212 and holes 214 are shown, a single set, multiple sets or other arrangements could be used instead.

There are several advantages of the disclosed rigid and flexible strip electrodes over isolated and/or small footprint electrodes proposed in prior art. First, the surface area of each electrode is maximized to improve overall connectivity around the wrist. Second, since each electrode touches the skin all around the wrist, its reliability of coming in contact with the skin at all times (for example, during sleep) is significantly higher. Finally, by forming a connection all around the wrist, the dependence of each electrode's performance on its physical position around the wrist is minimized. Therefore, the smart band pair described in this invention, by virtue of its rigid and flexible strip electrodes, is able to acquire good quality ECG data with a high degree of accuracy.

FIG. 4 illustrates an alternate view of the primary smart band showing the touchscreen display along with the straps, clasping mechanism, and flexible strip electrodes. The profile shape of the primary smart band straps 206, 208 is curved, and they provide a snug fit around the wrist using the stud 212 and hole 214 clasping mechanism. When worn around the wrist, the rigid strip electrodes (not shown) and the flexible strip electrodes 222, 224, 226 embedded in the straps 206, 208 make contact with the skin all around the wrist. The primary smart band is switched on by activating the on/off button 210. The touchscreen display 204 helps in visualizing ECG data and its analysis in real-time. In one example, the touchscreen display 204 displays real-time ECG waveform data along with HR/HRV metrics and pertinent alarms when these metrics are out of range. In another example, the user can interact with the touchscreen display 204 to perform tasks like reviewing historic ECG data and/or sending a distress signal to other connected users/devices.

FIG. 5 illustrates an alternate view of the secondary smart band showing the front cover along with the straps, clasping mechanism, and flexible strip electrodes. The profile shape of the secondary smart band straps 306, 308 is curved, and they provide a snug fit around the wrist using the stud 326 and hole 328 clasping mechanism. When worn around the wrist, the rigid strip electrodes (not shown) and the flexible strip electrodes 320, 322, 324 embedded in the straps 306, 308 make contact with the skin all around the wrist. The secondary smart band is switched on by activating the on/off button 310. In place of a touchscreen display, in this embodiment the secondary smart band is provided with a plastic front cover 304.

Figure 6:
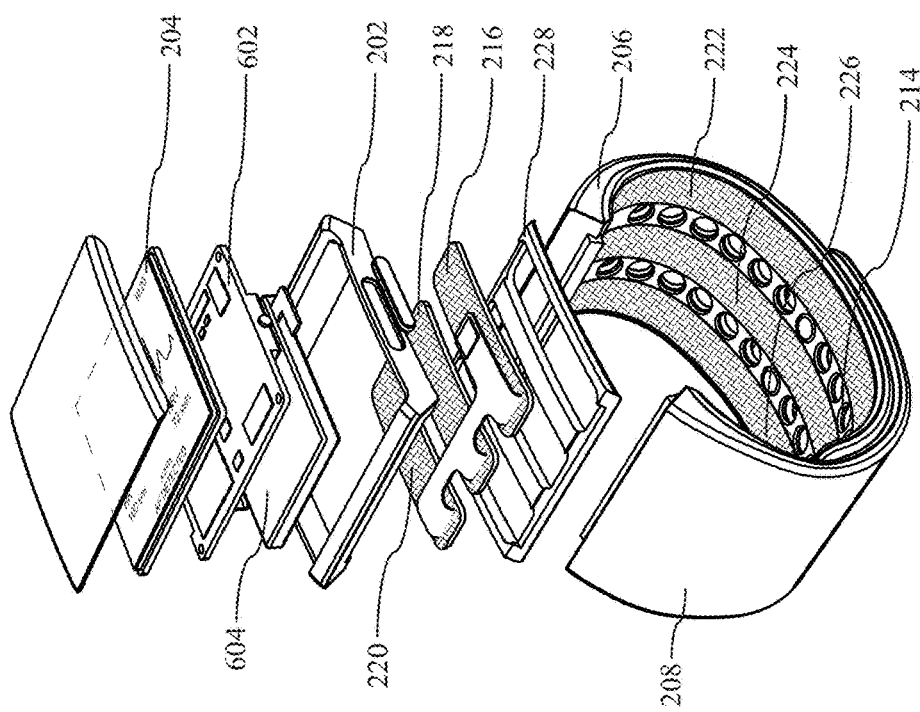
FIG. 6 illustrates an exploded view of the primary smart band showing the key components.

FIG. 6 illustrates an exploded view of the primary smart band showing the key components in one embodiment. These include a touchscreen display 204, printed circuit board 602 containing all related hardware and running the desired software, enclosure 202, rechargeable battery 604, backplate 228 with embedded rigid strip electrodes 216, 218, 220 and straps 206, 208 with flexible strip electrodes 222, 224, 226 and clasping holes 214.

Figure 7:
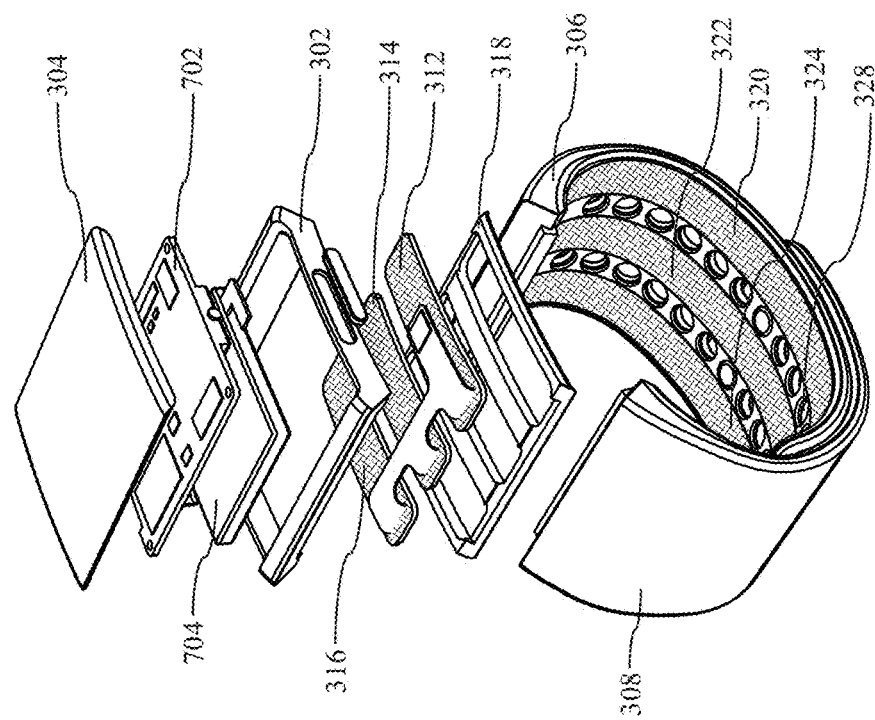
FIG. 7 illustrates an exploded view of the secondary smart band showing the key components.

FIG. 7 illustrates an exploded view of the secondary smart band showing the key components in one embodiment. These include a plastic front cover 304, printed circuit board 702 containing all related hardware and running the desired software, enclosure 302, rechargeable battery 704, backplate 318 with embedded rigid strip electrodes 312, 314, 316 and straps 306, 308 with flexible strip electrodes 320, 322, 324 and clasping holes 328.

In one example, desired components of the primary (FIG. 6) and secondary (FIG. 7) smart bands are provided with clipping mechanisms enabling them to be snap fitted.

Figure 8:
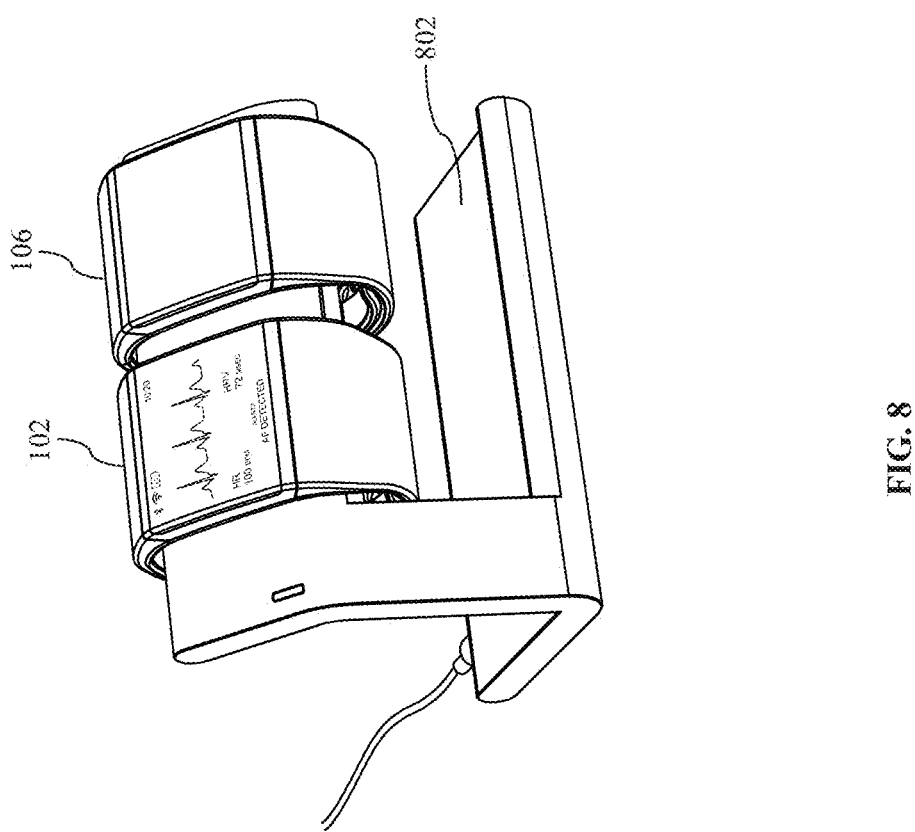
FIG. 8 illustrates the smart band pair being charged on a twin wireless charging unit.

FIG. 8 illustrates the smart band pair being charged on a twin wireless charging unit. Both primary 102 and secondary 106 smart bands are provided with rechargeable batteries 604, 704 and wireless charging hardware/software. The smart band pair 102, 106 can therefore be charged on a twin wireless charging unit 802. It will be appreciated that other charging arrangements, including wired, could also be used.

Figure 9:
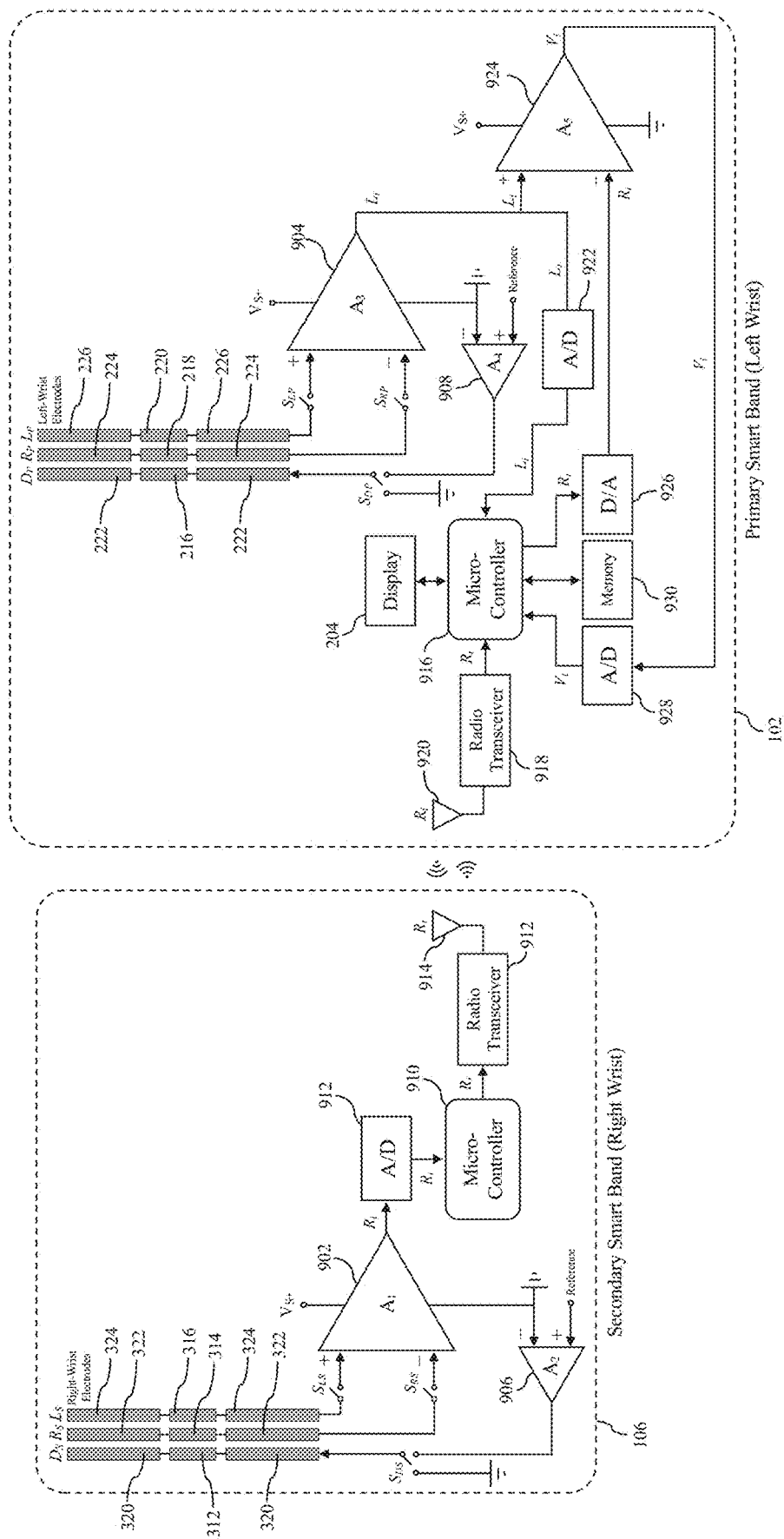
FIG. 9 illustrates an example operational diagram of the smart band pair.

FIG. 9 illustrates an example operational diagram of the smart band pair. Here, the reference electrode in each smart band is either a ground or RLD. Biopotential data from both smart bands is sent directly and also via a differential amplifier to the primary smart band's microcontroller for processing. In this example, the secondary smart band 106 is attached to a user's right wrist while the primary smart band 102 is attached to the user's left wrist.

In FIG. 9, in the secondary smart band 106, the three rigid strip electrodes 312, 314, 316 and the three flexible strip electrodes 320, 322, 324 are electrically connected. Similarly, in the primary smart band 102, the three rigid strip electrodes 216, 218, 220 and the three flexible strip electrodes 222, 224, 226 are electrically connected.

Referring to FIG. 9, the secondary smart band 106 comprises three strip electrodes namely ground or RLD 312, 320, right 314, 322, and left 316, 324 electrodes that are connected to biopotential amplification and conditioning circuitry 902 via three digital switches $S_{DS}$, $S_{RS}$, $S_{LS}$. Similarly, the primary smart band 102 comprises three strip electrodes namely ground or RLD 216, 222, right 218, 224, and left 220, 226 electrodes that are connected to biopotential amplification and conditioning circuitry 904 via three digital switches $S_{DP}$, $S_{RP}$, $S_{LP}$. The secondary smart band switches $S_{DS}$, $S_{RS}$, $S_{LS}$ are controlled by the secondary smart band microcontroller 910 while the primary smart band switches $S_{DP}$, $S_{RP}$, $S_{LP}$ are controlled by the primary smart band microcontroller 916.

In FIG. 9, $S_{DP}$ in the primary smart band 102 and $S_{DS}$ in the secondary smart band 106 are changeover switches with two binary states, namely, 0 and 1. In state 0, they convert their respective electrodes to ground electrodes via grounding whereas in state 1, they convert their respective electrodes to RLD electrodes via the amplifiers 906 and 908. This feature allows for various combinations of ground and RLD electrodes to be readily used in the primary and secondary smart bands to reduce noise and enhance ECG signal quality.

Referring to FIG. 9, switches $S_{RP}$ and $S_{LP}$ are provided for primary smart band strip electrodes 218, 224, 220, 226 and switches $S_{RS}$ and $S_{LS}$ are provided for secondary smart band strip electrodes 314, 322, 316, 324. Again, these switches have two binary states, namely, 0 and 1. A state 0 will remove these electrodes from the ECG monitoring circuit whereas a state 1 will connect these electrodes to the ECG monitoring circuit. This allows for different electrode configurations and connections to be used for each smart band to minimize signal-to-noise ratio (SNR), thus further enhancing ECG signal quality.

In one example, if states of $S_{DS}$, $S_{LS}$, $S_{RS}$, $S_{DP}$, $S_{LP}$, and $S_{RP}$ are 1, then secondary and primary smart band strip electrodes 314, 322, 316, 324, 218, 224, 220, and 226 will be involved in ECG data monitoring wherein the reference electrodes 312, 320, 216, and 222 will act as RLD electrodes. In another example, if states of $S_{DS}$, $S_{LS}$, and $S_{RP}$ are 0 while states of $S_{RS}$, $S_{DP}$, and $S_{LP}$ are 1, then secondary and primary smart band strip electrodes 314, 322, 220, and 226 will be involved in ECG data monitoring wherein the reference electrodes 312, 320 will act as ground electrodes and reference electrodes 216, 222 will act as RLD electrodes. In addition to reducing noise, the switching feature is also very useful for device testing and calibration whereby related hardware/software can be fine-tuned to obtain optimum signal quality.

In one embodiment, rapid switching of all six switches, namely, $S_{DS}$, $S_{LS}$, $S_{RS}$, $S_{DP}$, $S_{LP}$, and $S_{RP}$ is undertaken in such a manner that left and right side biopotential data is acquired, processed, and combined every data sampling period as the system continuously and repeatedly loops through all possible configurations of the switches. Since each switch has 2 states (0 and 1) and total number of switches are 6, there are $2^6=64$ unique configurations that are possible per data sampling period (FIGS. 10A-10B).

In one example, a truth table of the type shown in FIGS. 10A-10B is stored inside the primary smart band memory 930 with the pointer 1002 at configuration #1. As per configuration #1 row, the desired states of the secondary smart band switches $S_{LS}$, $S_{RS}$, and $S_{DS}$ are wirelessly transmitted by the primary smart band microcontroller 916 to the secondary smart band microcontroller 910 employing radio transceivers 918, 912 and antennas 920, 914. The secondary smart band microcontroller 910 then sets the states of switches $S_{LS}$, $S_{RS}$, and $S_{DS}$ based on the information received from the primary smart band microcontroller 916. At the same time, the primary smart band microcontroller 916 sets the states of switches $S_{LP}$, $S_{RP}$, and $S_{DP}$ as per configuration #1 row. Once all six switches are set to the states described by configuration #1 row, the secondary smart band 106 acquires biopotential data from the right wrist and transmits it wirelessly to the primary smart band 102 that also simultaneously acquires biopotential data from the from the left wrist. Then, the primary smart band microcontroller 916 moves the pointer 1002 to the next row on the truth table (FIGS. 10A-10B) and the above procedure of setting of states of all six switches and biopotential data acquisition is repeated. A new data sampling period begins when the pointer 1002 resets (reaches configuration #1 row) and ends when the pointer 1002 reaches configuration #64 row. In this manner, left and right side biopotential data is continuously acquired by the smart bands 102, 106 for all 64 switch configurations for every data sampling period.

In one example, the rapid switching described above can be undertaken by the primary smart band microcontroller 916 by utilizing its clock signal. In another example, a field programmable gate array (FPGA) module working in conjunction with the primary smart band microcontroller 916 can be employed to accomplish the rapid switching.

With reference to FIG. 9 and FIGS. 10A-10B, for each switch configuration, the right-side biopotential signal ($R_i$) measured by the secondary smart band electrodes 312, 320, 314, 322, 316, and 324 is acquired by the microcontroller 910 via an analog-to-digital (A/D) converter 912. Using the radio transceiver 912 and antenna 914, the microcontroller 910 wirelessly sends the right-side biopotential signal ($R_i$) to the primary smart band 102 attached to the user's left wrist. The primary smart band microcontroller 916 wirelessly receives the right-side biopotential signal ($R_i$) via its radio transceiver 918 and antenna 920. At the same time, the left-side biopotential signal ($L_i$) measured by the primary smart band electrodes 216, 222, 218, 224, 220, 226 is also acquired by the primary smart band microcontroller 916 via an A/D converter 922. Additionally, the left-side biopotential signal ($L_i$) is fed to the first terminal of a differential amplifier 924 inside the primary smart band 102. Moreover, the right-side biopotential signal ($R_i$) from the primary smart band microcontroller 916 is fed via a D/A converter 926 to the second terminal of the differential amplifier 924. The differential amplifier 924 output ($V_i$) is then acquired by the primary smart band microcontroller 916 via the A/D converter 928.

When biopotential data is acquired via the described switching method as a continuous stream and buffered over a period of time, there will be 64 right-side biopotential signals ($R_i$), 64 left-side biopotential signals ($L_i$), and 64 analog differential signals ($V_i$). The primary smart band microcontroller 916 can employ a number of techniques to aggregate and combine these 64 biopotential signals to produce higher fidelity biopotential signals. In one example, the 64 right-side biopotential signals ($R_i$) can be aggregated by computing their weighted mean using weights $W_{Ri}$ as per equation 1, whereby total switch configurations c=64:

$$V_R = \frac{\sum_{i=0}^{c-1} W_{Ri} R_i}{\sum_{i=0}^{c-1} W_{Ri}} \qquad (1)$$

Similarly, the 64 left-side biopotential signals ($L_i$) can be aggregated by computing their weighted mean using weights $W_{Li}$ as per equation 2, whereby total switch configurations c=64:

$$V_L = \frac{\sum_{i=0}^{c-1} W_{Li} L_i}{\sum_{i=0}^{c-1} W_{Li}} \qquad (2)$$

Finally, the 64 analog differential signals ($V_i$) can be aggregated by computing their weighted mean using weights $W_{Vi}$ as per equation 3, whereby total switch configurations c=64:

$$V_{Diff} = \frac{\sum_{i=0}^{c-1} W_{Vi} V_i}{\sum_{i=0}^{c-1} W_{Vi}} \qquad (3)$$

In another embodiment, $R_i$, $L_i$, and $V_i$ can be aggregated by employing a log product as per equations 4-6, whereby total switch configurations c=64:

$$V_R = \log\left(\prod_{i=0}^{c-1} R_i\right) \qquad (4)$$

$$V_L = \log\left(\prod_{i=0}^{c-1} L_i\right) \qquad (5)$$

$$V_{Diff} = \log\left(\prod_{i=0}^{c-1} V_i\right) \qquad (6)$$

With reference to FIG. 9 and aggregation equations 1-6, the primary smart band microcontroller 916 can employ various DSP techniques on the biopotential signals $V_R$ and $V_L$ to produce a high-fidelity ECG signal. In one example, a single-lead ECG signal ($ECG_{Digital}$) is synthesized by the primary smart band microcontroller 916 by computing the difference between the biopotential signals $V_R$ and $V_L$ as per equation 7:

$$ECG_{Digital} = (V_L - V_R) \qquad (7)$$

In another example, a single-lead ECG signal ($ECG_{Digital}$) is synthesized by the primary smart band microcontroller 916 by computing the weighted mean of the biopotential signals $V_R$ and $V_L$ using respective weights $W_R$ and $W_L$ as per equation 8:

$$ECG_{Digital} = \frac{(W_L V_L + W_R V_R)}{(W_L + W_R)} \qquad (8)$$

In yet another example, a single-lead ECG signal ($ECG_{Digital}$) is synthesized by the primary smart band microcontroller 916 by computing a convolution between the biopotential signals $V_R$ and $V_L$ as per equation 9, whereby n is the number of samples in the $V_R$ and $V_L$ arrays:

$$ECG_{Digital}[n] = V_R[n] * V_L[n] = \sum_{k=-\infty}^{\infty} V_R[k], V_L[n-k] \qquad (9)$$

As per FIG. 9 and aggregation equations 1-6, the primary smart band microcontroller 916 also synthesizes the signal $V_{Diff}$ which is the result of the analog signal amplification and conditioning of $R_i$ and $L_i$ via the differential amplifier 924. Therefore, the high-fidelity analog ECG signal ($ECG_{Analog}$), can be defined via equation 10 as follows:

$$ECG_{Analog} = V_{Diff} \qquad (10)$$

$ECG_{Digital}$ (equations (7)-(9)) and $ECG_{Analog}$ (equation (10)) represent high-fidelity ECG signals that are obtained via two very distinct and complementary techniques—DSP and analog signal conditioning respectively.

In one example, the primary smart band microcontroller 916 (FIG. 9) combines and fuses the $ECG_{Digital}$ and $ECG_{Analog}$ signals to further suppress noise and obtain an even higher quality and fidelity signal, namely, $ECG_{Fusion}$ as per equation 11:

$$ECG_{Fusion} = \sqrt{(ECG_{Digital})^2 (ECG_{Analog})^2} \qquad (11)$$

There are several other ways by which $ECG_{Fusion}$ can be computed. In one example, $ECG_{Fusion}$ is computed as an arithmetic mean of $ECG_{Digital}$ and $ECG_{Analog}$ as per equation (12):

$$ECG_{Fusion} = \frac{ECG_{Digital} + ECG_{Analog}}{2} \qquad (12)$$

Figure 11:
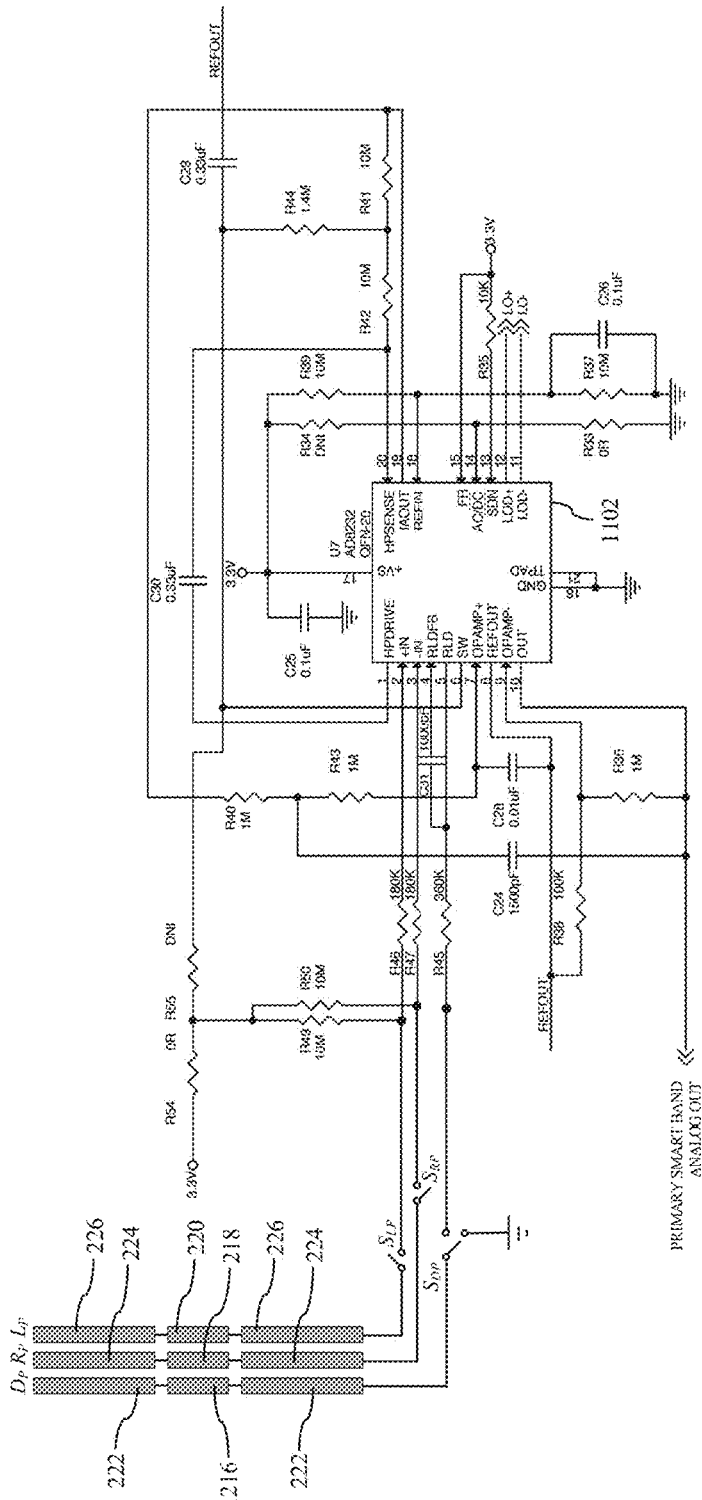
FIG. 11 illustrates an example circuit diagram of a biopotential amplifier with a ground/RLD strip electrode implemented using Analog Devices AD8232 chip.

FIG. 11 illustrates an example circuit diagram of a biopotential amplifier with a ground/RLD strip electrode implemented using Analog Devices AD8232 chip. The biopotential amplifiers described in FIG. 9, can be easily implemented using commercially available ECG analog front ends like the AD8232 chip 1102. The disclosed circuit diagram shows the values of various electronic components and the primary smart band strip electrodes 216, 222, 218, 224, 220, 226 connected to the AD8232 chip 1102.

Figure 12:
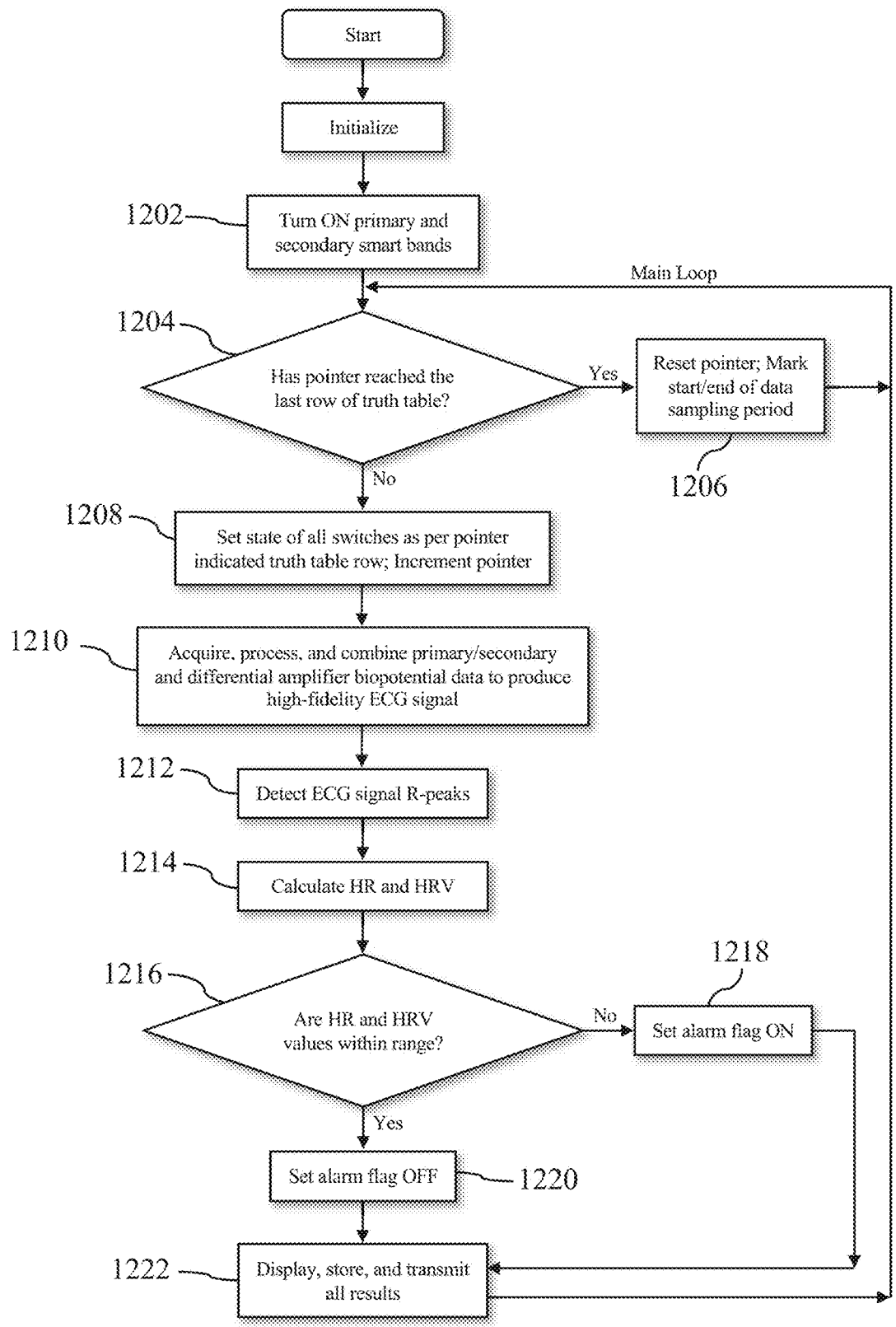
FIG. 12 illustrates a flowchart depicting one example method of continuous high-fidelity ECG monitoring and HR/HRV analysis via electrode switching.

FIG. 12 illustrates a flowchart depicting one example method of continuous high-fidelity ECG monitoring and HR/HRV analysis via electrode switching. At step 1202 both primary 102 and secondary 106 smart bands are switched on using buttons 210 and 310. At step 1204 the microcontroller 916 inside the primary smart band checks whether the pointer 1002 has reached the end of the truth table stored inside the primary smart band memory 930. If pointer 1002 has not reached the end of the truth table at step 1204, then at step 1208, the states of all six switches are set as per the row indicated by the pointer, biopotential data acquisition is initiated, and the pointer is incremented by 1. However, if pointer 1002 has reached the end of the truth table at step 1204, then, at step 1206, the pointer is reset, and start/end of a sampling period is marked. The above procedure continues in the main loop for all pointer positions and resets. At step 1210, the primary smart band microcontroller 916 performs various operations on the received biopotential data like processing, aggregation, and fusion to produce high-fidelity ECG data. At step 1212, the primary smart band microcontroller 916 detects ECG R-peaks and then at step 1214 it computes metrics like HR and HRV. In this example, at step 1216, the primary smart band microcontroller 916 checks the calculated HR/HRV metrics against predefined acceptable values. Based on whether the calculated HR/HRV parameters are in range or out of range, alarm flags are accordingly set at steps 1218 and 1220. At step 1222, the primary smart band touchscreen display 204 displays ECG data and related analytics along with the alarm status in real-time. Moreover, at step 1222, the primary smart band wirelessly transmits all ECG data and related analytics to third-party devices 110.

Figure 13:
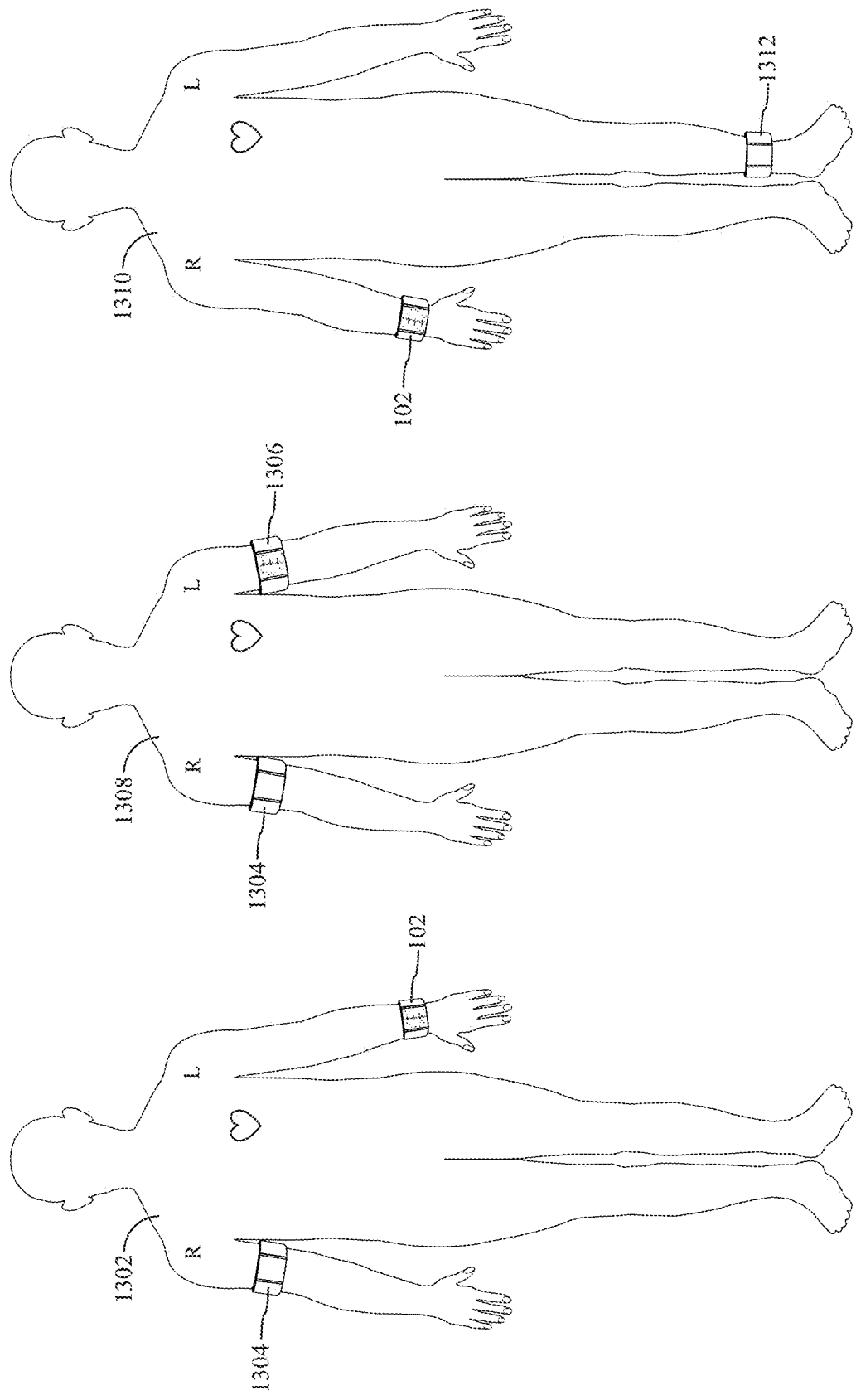
FIG. 13 illustrates examples of various locations on the human body where wearables employing the underlying design and principle of the current invention can be attached to undertake continuous leadless ECG monitoring.

FIG. 13 illustrates examples of various locations on the human body where wearables employing the underlying design and principle of the current invention can be attached to undertake continuous leadless ECG monitoring. As illustrated at 1302, the primary smart band 102 can be worn around the left wrist while a secondary smart band 1304 can be worn around the right upper arm. As illustrated at 1308, a primary smart band 1306 can be worn around the left upper arm while the secondary smart band 1304 can be worn around the right upper arm. Finally, as illustrated at 1310, the primary smart band 102 can be worn around the right wrist while a secondary smart band 1312 can be worn around the left ankle. These examples demonstrate that the disclosed wireless smart band pair and/or other similar wearable pair can be attached at various locations along the four limbs to accomplish leadless Einthoven-type single-lead ECG measurements.

It will be appreciated by one skilled in the art that variants can exist in the above-described arrangements and applications.

For example, in one embodiment, the described smart band pair can also be used for intermittent ECG monitoring and analysis. For example, the user can operate the on/off switches 210, 310 on the primary and secondary smart bands 102, 106 to enable and disable ECG data acquisition and analysis as required. In another example, the microcontrollers 910, 916, inside the primary and secondary smart bands 102, 106 can be programmed to acquire and analyze ECG data at predefined intervals, for example, acquire and analyze ECG data for 5 minutes every 30 minutes.

In another embodiment, the described smart band pair can be used solely for biopotential data acquisition and transmission while all data processing/analysis can be done on external devices. For example, the primary smart band 102 can acquire and wirelessly transmit the first biopotential data to a smartphone and the secondary smart band 106 can acquire and wirelessly transmit the second biopotential data to the same smartphone. This smartphone can then process and combine the received first and second biopotential data to produce a high-fidelity ECG signal. The smartphone can also perform further analyses on the ECG signal like R-peak detection, HR/HRV evaluation, and alarm generation. The smartphone can be replaced by a laptop, tablet, and/or any similar computing device.

The specific examples provided herein relate to a continuous leadless electrocardiogram monitor, however, the materials, methods of application and arrangements of the invention can be varied. The scope of the claims should not be limited by the preferred embodiments set forth in the examples but should be given the broadest interpretation consistent with the description as a whole.

What is claimed is:

1. An electrocardiogram monitor comprising:
   (a) a primary smart band having a primary microcontroller, at least three electrodes, and at least one digital switch per electrode to enable or disable the electrode during data acquisition, wherein the at least three electrodes are configured to contact skin of a user and measure a first high-fidelity biopotential signal;
   (b) a secondary smart band having a secondary microcontroller, at least three electrodes, and at least one digital switch per electrode to enable or disable the electrode during data acquisition, wherein the at least three electrodes are configured to contact the skin of the user and measure a second high-fidelity biopotential signal;
   (c) wherein the primary and secondary microcontrollers control the digital switches to repeatedly loop through all possible configurations of the digital switches and acquire first and second high-fidelity biopotential signals for each of the configurations;
   (d) wherein, for each of the configurations of the digital switches, the secondary microcontroller digitizes the second high-fidelity biopotential signal to produce a second digitized signal and transmits the second digitized signal wirelessly to the primary smart band;
   (e) wherein, for each of the configurations of the digital switches, the primary microcontroller wirelessly receives the second digitized signal from the secondary smart band, and digitizes the first high-fidelity biopotential signal to produce a first digitized signal;
   (f) wherein the primary microcontroller aggregates the first and second digitized signals for all of the switch configurations and employs DSP techniques on the aggregated first and second digitized signals to produce a first high-fidelity ECG waveform signal;
   (g) wherein the primary smart band further comprises a D/A module to convert the second digitized signal to an analog signal; and a differential amplifier which, for each of the configurations of the digital switches, receives as inputs the analog signal from the D/A module and the first high-fidelity biopotential signal and outputs a high-fidelity differential signal via analog signal conditioning and amplification;
   (h) wherein the primary microcontroller digitizes and aggregates the high-fidelity differential signal for all of the switch configurations to produce a second high-fidelity ECG waveform signal; and
   (i) wherein the primary microcontroller employs data fusion techniques to combine the first and second high-fidelity ECG waveform signals to produce a higher quality and fidelity ECG waveform signal.

2. The electrocardiogram monitor of claim 1 wherein at least one of the three electrodes of the primary and secondary smart bands include a reference electrode and the digital switches for the reference electrodes are changeover switches that allow these reference electrodes to be used either as RLD or ground electrodes during data acquisition to further improve ECG waveform signal quality and fidelity.

3. The electrocardiogram monitor of claim 1 wherein the primary and secondary smart bands each further comprise:
   an enclosure having a backplate; and
   straps connected to the enclosure,
wherein the at least three electrodes of the primary and secondary smart bands further comprise:

at least three rigid strip electrodes provided on each of the backplates of the primary and secondary smart bands; and at least three flexible strip electrodes provided on each of the straps;

wherein the at least three rigid strip electrodes are electrically connected to respective electrodes of the at least three flexible strip electrodes to maximize electrode contact area and eliminate dependency on electrode position around a limb of the user to enhance ECG waveform signal quality.

4. The electrocardiogram monitor of claim 1 wherein the primary smart band and secondary smart band comprise separate power sources.

5. The electrocardiogram monitor of claim 1 further comprising data storage in the primary smart band for storing the ECG signal and related information.

6. The electrocardiogram monitor of claim 1 further comprising a radio transceiver and antenna in the primary smart band or the secondary smart band for transmitting the ECG signal and related information to a separate computing device.

7. The electrocardiogram monitor of claim 6 wherein the computing device is selected from one consisting of a mobile device, smartphone, tablet, laptop, and computer.

8. The electrocardiogram monitor of claim 1 further comprising a display in the primary smart band configured to display information to the user.

9. The electrocardiogram monitor of claim 8 wherein the displayed information is selected from one or more of the group consisting of time, date, battery strength, wireless connectivity strength, Bluetooth status, HR, HRV, ECG waveform and alarm status.

10. The electrocardiogram monitor of claim 8 further comprising an alarm in the primary smart band, wherein the first microcontroller computes HR and HRV data and triggers and displays the alarm if the HR and/or HRV data are beyond pre-determined thresholds.

11. The electrocardiogram monitor of claim 8 wherein the display is a touchscreen display that is configured to receive inputs from the user.

12. The electrocardiogram monitor of claim 1 wherein the smart bands are smartwatches.

13. The electrocardiogram monitor of claim 1 further comprising a twin wireless charger for charging the primary smart band and secondary smart band.

14. The electrocardiogram monitor of claim 1 wherein the primary and secondary smart bands are configured to be attached at various locations along limbs of the user.

* * * * *